United States Patent
Twerdochlib

(12) 
(10) Patent No.: US 8,096,184 B2
(45) Date of Patent: Jan. 17, 2012

(54) TURBINE BLADE FOR MONITORING BLADE VIBRATION

(75) Inventor: Michael Twerdochlib, Oviedo, FL (US)

(73) Assignee: Siemens Energy, Inc., Orlando, FL (US)

( * ) Notice: Subject to any disclaimer, the term of this patent is extended or adjusted under 35 U.S.C. 154(b) by 905 days.

(21) Appl. No.: 10/881,798

(22) Filed: Jun. 30, 2004

(65) Prior Publication Data

US 2006/0000283 A1    Jan. 5, 2006

(51) Int. Cl.
*G01H 9/00* (2006.01)
(52) U.S. Cl. ................ 73/655; 73/593; 73/660
(58) Field of Classification Search .......... 73/655, 73/660, 593
See application file for complete search history.

(56) References Cited

U.S. PATENT DOCUMENTS

| | | | | |
|---|---|---|---|---|
| 4,573,358 A | * | 3/1986 | Luongo | 73/660 |
| 4,896,537 A | * | 1/1990 | Osborne | 73/660 |
| 5,097,711 A | * | 3/1992 | Rozelle et al. | 73/660 |
| 5,365,663 A | * | 11/1994 | Demartini | 29/889.21 |
| 5,479,826 A | * | 1/1996 | Twerdochlib et al. | 73/660 |
| 5,511,426 A | * | 4/1996 | Clement et al. | 73/655 |
| 5,761,956 A | * | 6/1998 | Beeson et al. | 73/660 |
| 6,945,114 B2 | * | 9/2005 | Kenderian et al. | 73/643 |
| 7,775,114 B2 | * | 8/2010 | Twerdochlib et al. | 73/660 |

FOREIGN PATENT DOCUMENTS

GB    2342988 A    *    4/2000

* cited by examiner

*Primary Examiner* — J M Saint Surin

(57) ABSTRACT

The claimed invention provides a blade vibration measuring system comprising a blade, a transmitter, a target with non parallel edges located on the blade shroud and a receiver. The present invention also provides a blade adapted for measuring blade vibration. Furthermore, the claimed invention provides a method for monitoring blade vibration.

29 Claims, 5 Drawing Sheets

TURBINE BLADE FOR MONITORING BLADE VIBRATION

FIELD OF INVENTION

The present invention relates generally to blade vibration monitoring and, more particularly, to blade vibration monitoring of a shrouded turbine blade.

BACKGROUND OF INVENTION

Turbo-machinery engines, such as combustion turbine engines, contain rotating blades in a compressor section and rotating blades in a turbine section. The blades are generally arranged circumferentially in rows with each row being comprised of a plurality of blades. Typical geometries include free standing blades (i.e. blades that do not contact adjacent blades) or shrouded blades (i.e. blades that do contact adjacent blades).

During normal engine operation, the rotating blades are exposed to excitation due to dynamic conditions in the engine such as flow induced vibration and nozzle effects. These dynamic conditions can lead to blade vibration, which is an appreciable cause of excitation failure in turbo-machinery.

A known means to avoid excitation failure is by monitoring operating blade vibration using a combination of strain gauges, non-contact capacitance probes, or optical probes to measure the vibration. However, such monitoring and evaluation is both costly and time inefficient.

Another known method involves a target painted on top of a blade shroud. However, these painted targets are problematic because they cannot detect motion in all directions. More specifically, blade tip motion parallel to the detecting edges of the target cannot be discerned.

Although several techniques exist for vibration measurements of rotating bladed-disk assemblies, no technique provides a suitable description of the dynamic behaviour. Therefore, there exists a need in the field of technology of turbomachinery for a method and device that can accurately, easily, and/or efficiently measure and monitor rotating blade vibration.

SUMMARY OF INVENTION

The present invention provides a system for monitoring rotating blade vibration, comprising a blade, a target with a first indicating edge and a second indicating edge, the first and second indicating edges being nonparallel and arranged on top of the blade, a receiving device adapted to receive data about the target, and a processor that interprets the received data or information from the receiving device.

The present invention also provides a blade adapted for measuring blade vibration, comprising, a root portion, a platform portion, an airfoil portion, and a target with a first indicating edge and a second indicating edge, the first indicating edge and the second indicating edge being non-parallel.

Furthermore, the present invention provides a method for monitoring vibration of a blade, comprising, connecting a target to a blade tip, passing the target through a first transmission signal field of a transmission device at a fist moment in time, reflecting the transmission signal from the target to a receiver at a second moment in time, and processing the first and second received signals.

BRIEF DESCRIPTION OF THE DRAWINGS

The above mentioned and other concepts of the present invention will now be described with reference to the drawings of the exemplary and preferred embodiments of the present invention. The illustrated embodiments are intended to illustrate, but not to limit the invention. The drawings contain the following figures, in which like numbers refer to like parts throughout the description and drawings and wherein.

DETAILED DESCRIPTION OF INVENTION

Figure 1:
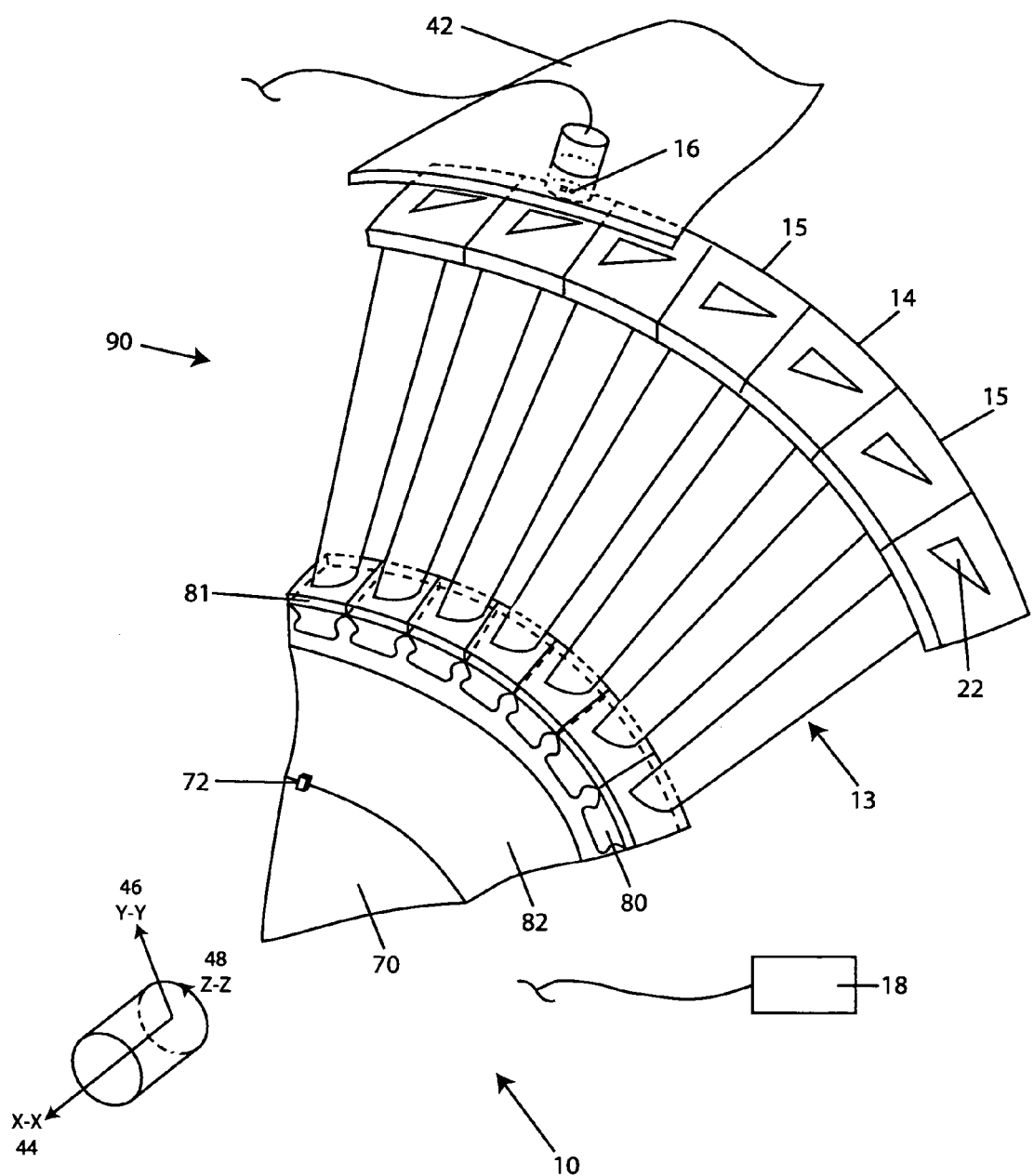
FIG. 1 is a perspective view of a section of a row of shrouded turbine blades operatively connected to the monitoring system of the present invention.

The monitoring system 10 described herein employs some basic concepts. For example, one concept relates to a monitoring system 10 that measures the frequency and amplitude of turbine blade 17 vibration, and monitors the vibration of the turbine blade 17. Another concept relates to a turbine blade 17 adapted for used with the monitoring system 10. Yet another concept relates to the processing of turbine blade 17 vibration signal information into usable computer output 60.

The present invention is disclosed in context of use as a monitoring system 10 within a combustion turbine engine for monitoring vibration of rotating turbine blades 17. The principles of the present invention, however, are not limited to use within combustion turbine engines or to monitor vibration of rotating turbine components. For example, the monitoring system 10 can be used in other operational monitoring environments to measure blade turbine 17 vibration, such as steam turbines, aero-thermal aircraft engines, electric generators, air or gas compressors, auxiliary power plants, and the like. Also, while the system 10 is described in context of use as a monitoring system 10 it is not limited to use as a monitoring system 10. For example, it can be used to obtain frequency and amplitude of blade 17 vibration for verification of analytic models and analysis of the turbine blades 17. One skilled in the art may find additional applications for the apparatus, processes, systems, components, configurations, methods and applications disclosed herein. Thus, the illustration and description of the present invention in context of an exemplary combustion turbine engine for monitoring vibration of rotating turbine or compressor components is merely one possible application of the present invention. However, the present invention has particular applicability for use as a monitoring system 10 for monitoring vibration of turbine components.

To assist in the description of the claimed invention and its operation, the following coordinate system is introduced. The X-X axis 44 defines the axial direction and extends in the direction of the rotor centerline. Axis Y-Y 46 defines the radial direction and extends radially in a radial plane that is perpendicular to the axial direction and outward through the blade 17. The Z-Z axis 48 defines the tangential direction and extends in the above radial plane being orthogonal to both the X-X axis 44 and Y-Y axis 46 and in the direction of rotation.

Two directions of vibration that the monitoring system 10 can measure and detect are the tangential and axial components of vibration. As one skilled in the art will recognize, these directions of vibration describe two fundamental blade modes. The tangential vibratory motion is determined by monitoring blade tip 28 motion in the Z-Z direction 48 and the axial vibratory motion is obtained by monitoring blade tip 28 motion in the X-X direction 44.

Components

Referring to FIG. 1, an exemplary monitoring system 10 adapted to monitor turbine blade 17 vibration is provided. The monitoring system 10 advantageously comprises a light beam 20 transmitted by a laser 16 and directed toward an optically reflective target 22 located on the shroud 14 of a turbine blade 17. As the target 22 moves through the light beam field 20, the light beam 20' is reflected back to a receiver 50 which then sends the reflected light beam 20' data to a processor 18. From the light beam data 20, 20', the processor 18 calculates the frequency, amplitude, and phase of vibration of the blade 17 as will be discussed in greater detail below. The processed information can then be viewed on a computer screen 40 using conventional computer program applications and/or saved.

Still referring to FIG. 1, a turbine blade 17 of the present invention is preferably comprised of four sub components: a blade root 80, a platform 81, an airfoil 12, and a shroud 14. The blade root 80 connects the blade 17 to the rotor 70 and may provide a conduit to transfer cooling flow from the rotor 70 to the blade 17. The platform 81 provides a transition from the blade root 80 to the blade airfoil 12. The platform also transfers cooling air from the blade root 80 to the blade airfoil 12. The platform 81 advantageously provides sealing between the combustion gas traversing the gas path and the cooling fluid in the rotor disk cavity 82 and can damp vibration for the bladed disk 90 system. The blade airfoil 12 directs the working fluid that creates a change in fluid momentum that causes the rotor 70 to rotate. The shroud 14 is located on top of the blade airfoil 12 at the blade tip 28 and is preferably integral to the blade airfoil 12. The shroud 14 also functions as a seal preventing leakage of the hot combustion gas over the shroud 14 and into the cylinder 42. Free standing blades 29 are conventionally distinguished from shrouded blades in that they do not have a shroud 14. Turbine blades 17 are typically monolithic structures fabricated or cast from metallic material such as super-alloys or ceramic materials such as ceramic matrix composites.

Figure 2A:
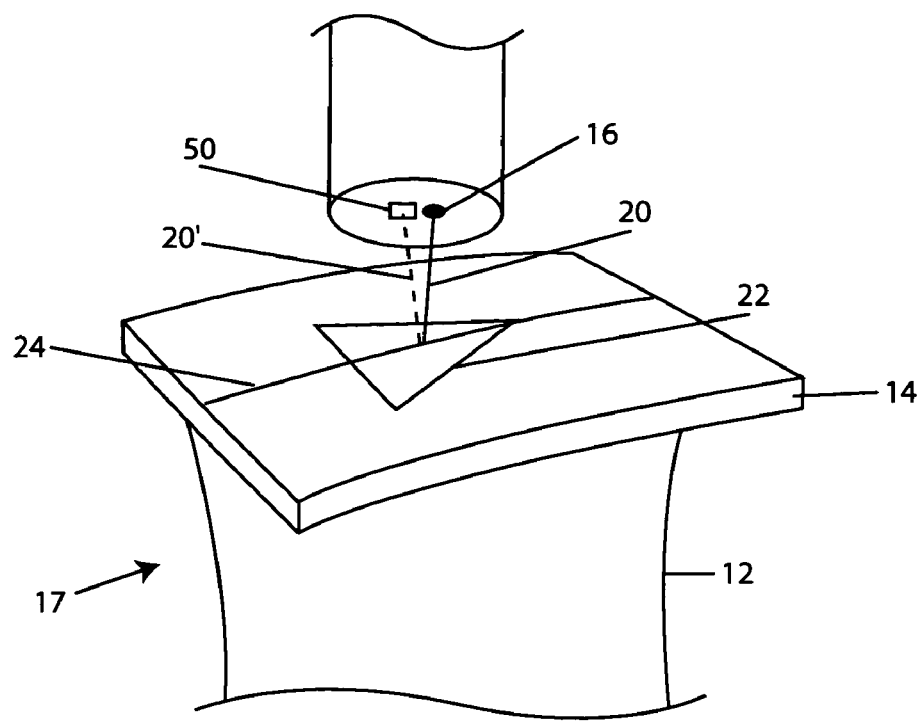
FIG. 2a is a perspective view of a shrouded blade tip with a target on the shroud.
Figure 2B:
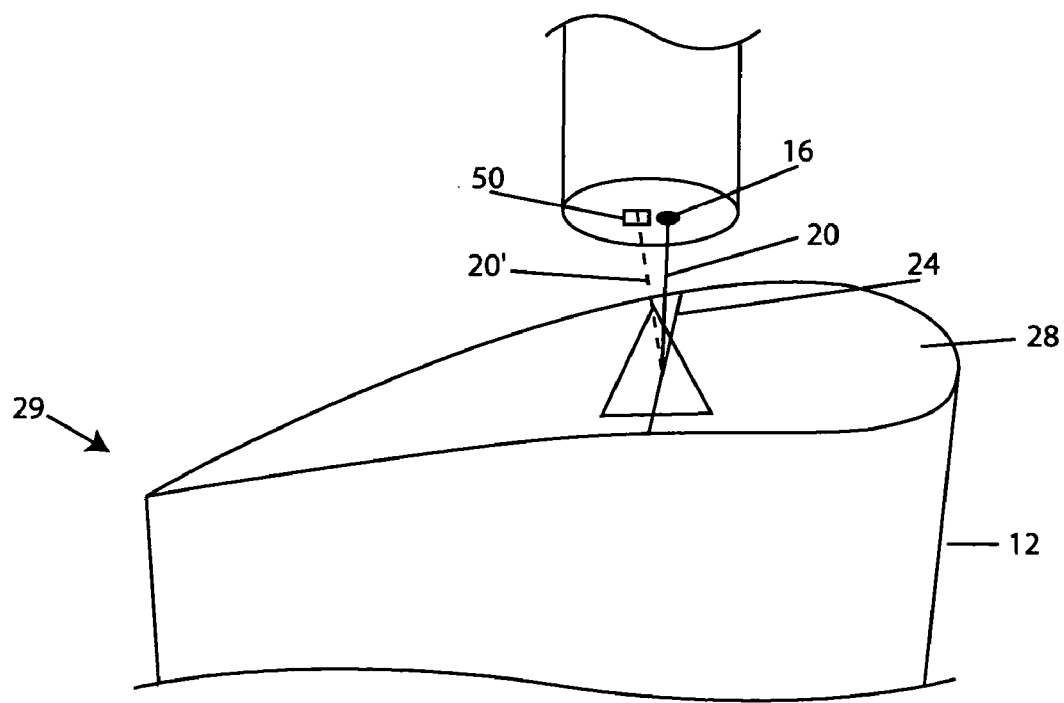
FIG. 2b is a perspective view of a free standing blade tip with the target on the blade tip.

As shown in FIGS. 2a and 2b, the monitoring system 10 can be used with free standing blades 28 as well as shrouded blades 17. If a shrouded blade 17 is used, typical arrangements include multiple blades 12 grouped by a single shroud segment 14, as well as integrally shrouded blades 17. If an integrally shrouded blade 17 arrangement is used, each blade 12 advantageously has an individual portion of shroud 14 operatively connected to adjacent blade shrouds 15.

Figure 2C:
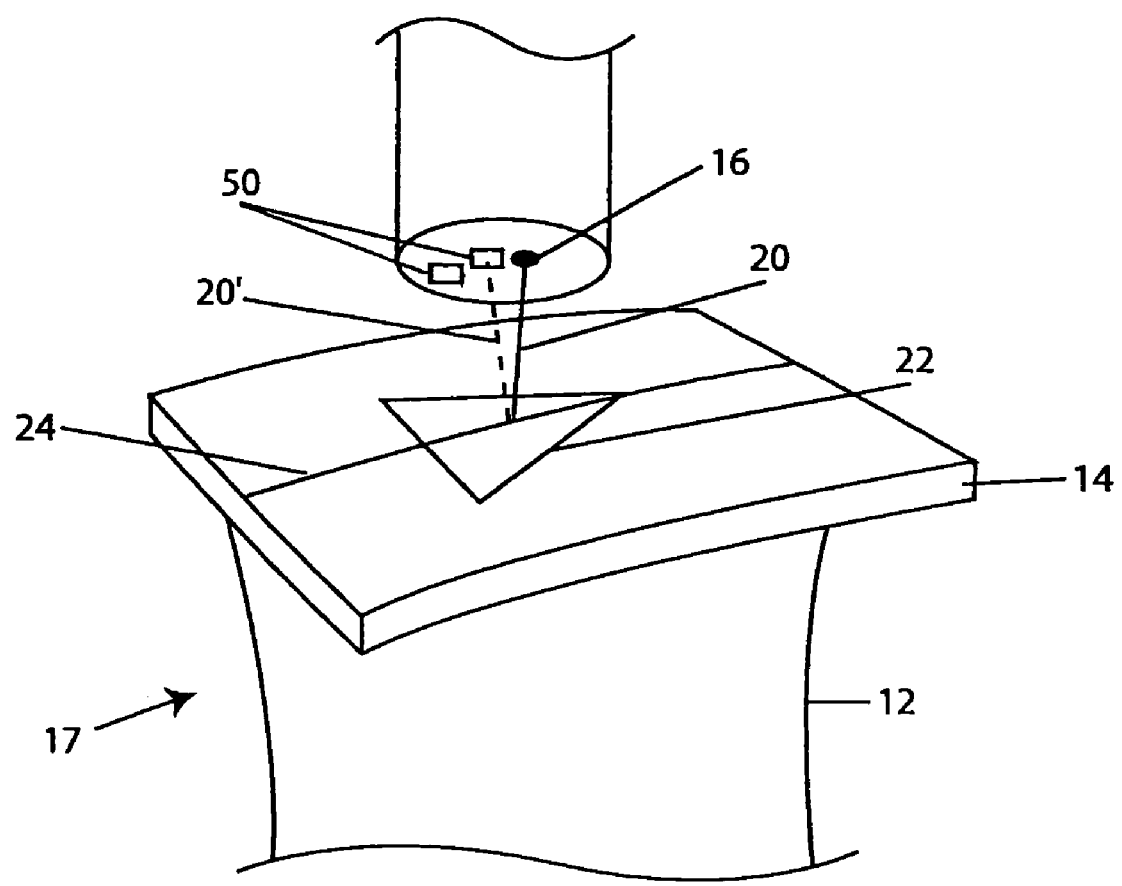
FIG. 2c is a perspective view of a shrouded blade tip with a target on the shroud and showing a plurality of receivers.

Referring back to FIGS. 1 and 2, a transmitter 16 generates a field through which the target 22 passes. The term "field" refers to the phenomenon generated by the transmitter 16. For example, if a laser 16 is used as the transmitter 16, the field is a light beam 20. Likewise, if a magnet 16 is used as the transmitter 16, the field is the magnetic field generated by the magnet 16. For another example, if a radar 16 is used as the transmitter 16, the field generated can be a microwave or any other electromagnetic wave.

In addition to the active transmitters described above, a transmitter free passive infra-red (IR) systems that function only as a receiver can also be employed to detect a change in the emission of thermal IR radiation as the probe focal point (detection spot) passed over the shroud 14 or target 22 surface. A target 22 used with a passive receiver is generally designed to emit less IR because the target is constructed from a material having a low emissitivity.

The illustrated transmitter 16 is embodied as an external laser and produces a light beam 22 of a suitable wavelength, preferably in the infrared band and at a few hundreds of milliwatts to produce a relatively small and intense spot on the shroud. A suitable laser 16 is commercially available from Agilis, West Palm, Fla. and as part number PC28-13G. However, as will be appreciated by those skilled in the art, other suitable transmitters 16 can be used.

If a laser is used as the transmitter, the laser 16 advantageously generates and projects a light beam 20 toward the blade shroud 14 or blade tip 28 if used with a free standing blade 29. The laser 16 may generate and emit the light beam 20 continually, randomly, intermittently, graduated, or otherwise, although continuous emission is preferred for a more robust monitoring of the turbine blades 17. A light beam 20 with a smaller diameter is preferred because it 20 responds most quickly to the arrival of the first indicating edge (e.g. arriving edge) 38 and departure of the second indicating edge 32 (e.g. departing edge) as the spot transits the target 22, as well as having increased light spot intensity, thus improving the accuracy of the measurement of blade tip 28 displacement and provides for more precise detection of the arrival of the first 38 and departure of the second 32 indicating edges of the target 22.

The receiver 50 receives the reflected field 20' and converts the reflected field 20' to a useable electrical signal and is sent to the processor 18. If the field 20 is a light beam 20, the receiver 50 can detect a reflected light beam 20'. If the field 20 is a magnetic field 20, the receiver 50 should detect a perturbation in this beam 20' produced by the target 22 on the shroud 14. If the field 20 is a microwave 20, receiver 50 can detect a reflected microwave. However, as would be appreciated by those skilled in the art, other suitable receivers 50 are acceptable such as magnetic receivers 50 or microwave receivers 50. If the receiver is used to detect a reflected light beam 20', a plurality of receivers 50 arranged to at least partially surround the laser 16 is preferably used to increase the likelihood of reflected field detection although there is no requirement to use a plurality of receivers or to arrange the receivers in a particular pattern. The transmitting device 16 may also function as the receiver 50.

Figure 3A:
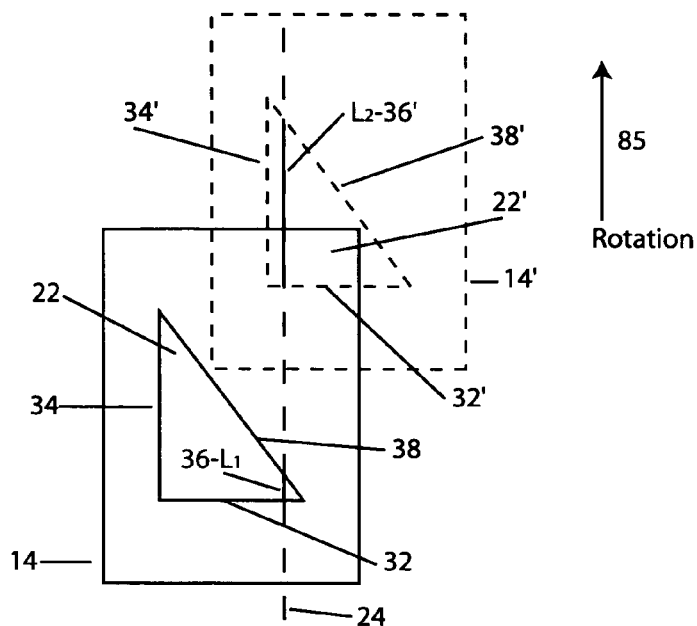
FIG. 3a is a plan view of the target on a shroud section at a first moment in time and the displaced target on a displaced shroud at a second moment in time.
Figure 3B:
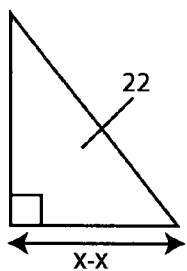
FIG. 3b-3i are plan views of exemplary target geometries.
Figure 3C:
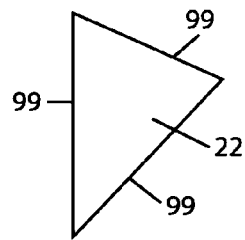
Figure 3D:
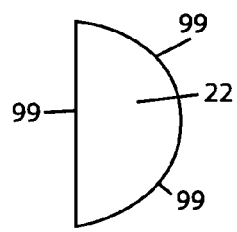
Figure 3E:
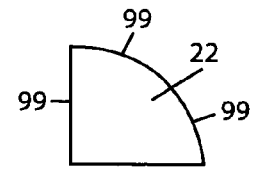
Figure 3F:
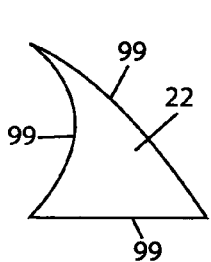
Figure 3G:
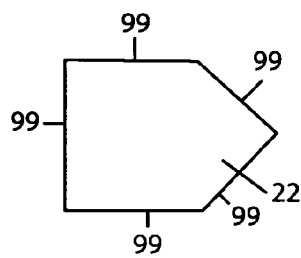
Figure 3H:
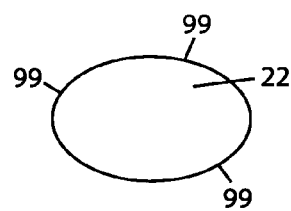
Figure 3I:
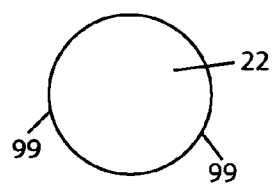
Figure 4:
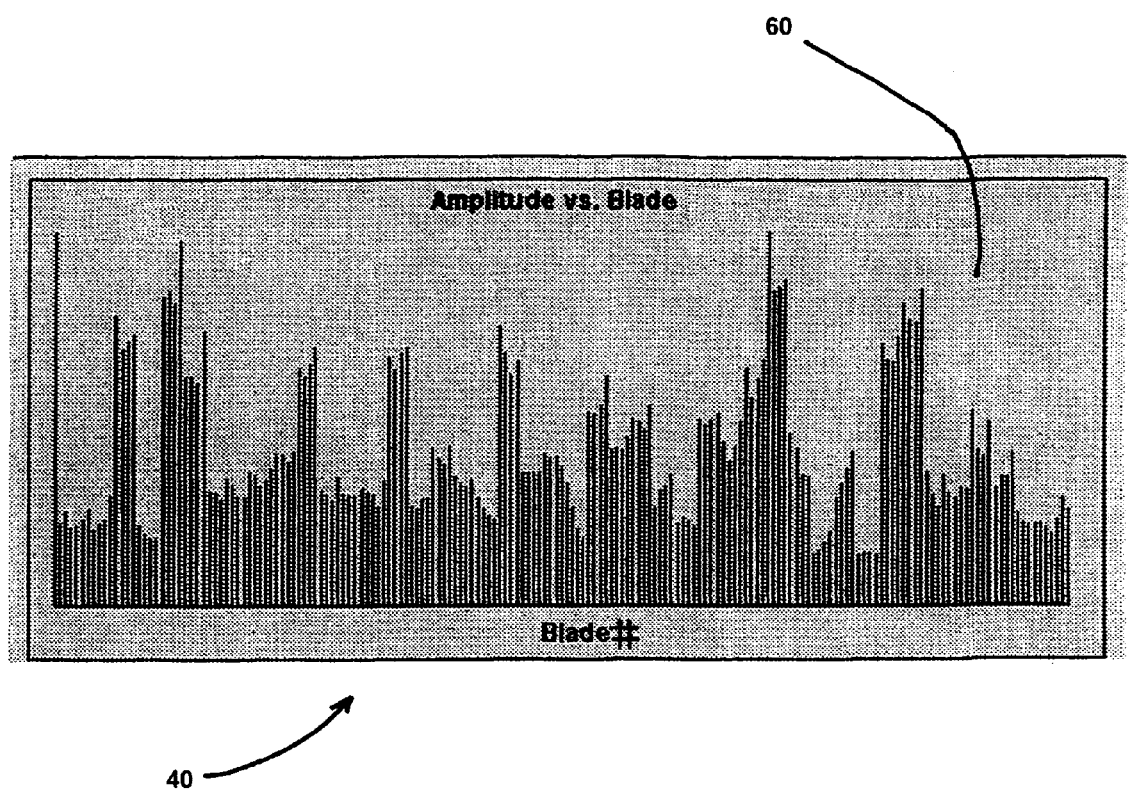
FIG. 4 is an exemplary computer screen display of processed information obtained from the monitoring system.

As shown in FIG. 2a, the target 22 is adapted to pass through the field 20 generated by the transmitter 16 and reflect a portion of the field 20' back toward the receiver 50 or otherwise alter the transmitted field. Referring to FIG. 3a, the target 22 has two nonparallel edges 32, 38 that allows for detection of linear motions of the shroud 14 parallel to X-X axis 44 and Z-Z axis 48. The target 22 edge or edges are formed by the target 22 perimeter which defines its physical shape. For example, if the target is comprised of one or more linear segments then edges are formed by the linear segments. Thus if the target is a triangle (See FIG. 3a), then three edges are respectively formed by the three sides of the triangle. For another example, if the target is comprised of one or more arcuate segments then edges are formed by one or more portions of the arcuate segments. Thus if the target is an oval (See FIG. 3h), then one or more edges may be formed along the arc bounded by the major axis and one or more of edges may be formed along the arc bounded by the minor axis. Of course, the target may comprise both linear and arcuate portions, and thus have a both linear-based edges and arcuate-based edges.

The target 22 is preferably triangular, more preferably right triangular, in shape since triangles have the minimum number of edges that can be geometrically configured with at least two non parallel edges 32, 38. Reducing the number of edges minimizes the processing of extraneous information since only non parallel edge 32, 38 data needs to be collected in order to determine the blade 17 vibration. However, there is no requirement that the target 22 be triangular in shape and FIGS. 3b-3g provide some suitable exemplary configurations comprising at least two non parallel edges 99. Targets 22 having straight indicating edges 99 provide a vibration measurement independent of the axial position of the transmitter 16 relative to the axial position of the shroud 14. This relative offset between transmitter 16 and shroud 14 can be up to several inches in length when used in large turbines, preferably approaching 0.5 inch.

The target 22 advantageously reflects the transmitted field 20 toward the receiver 50. If the transmitter 16 is a laser 16, the target can be made of a reflective paint, tape, plate, ceramic, and the like. If the transmitting device 16 is a magnetic transmitter 16, the target 22 can be made of a ferrous material capable of reflecting the magnetic field 20' toward the receiver 50 or otherwise altering 20'. If a microwave transmitter is used, target 22 can be made of a material that reflects the microwave field 20 toward the receiver 50, reduces such reflection, or changes the phase of the reflected field 20'. Referring to FIG. 2b, if the target 22 is placed on the blade tip 28 of a free standing blade 29, the size of target 22 may be limited to fit onto the blade tip 28 since the free standing blade 29 tips 28 tend to be relatively thin in the Z-Z 48 direction.

Referring again to FIG. 1, a rotation monitoring device 72 is advantageously attached to the rotor 70 or other suitable location, to count the number of rotor 70 revolutions. Such devices 72 may perform the counting function based upon optics, magnets, physical contact, other phenomenon and the like. A suitable optical rotation monitoring device is available from the Motion Sensors, Inc. From the information collected from the rotation monitoring device 72, each target 22 in the blade row 13 can be identified and associated with a particular blade 17 in the blade row 13.

Referring back to FIG. 3a, the processor 18 is configured to compare the actual time the second indicating edge 32' of the target 22 departs or exits the field 20 with the expected time that the second indicating edge 32 of the target 22 is expected to depart or exit the field 20 in the absence of vibration. The processor is also configured to compare the actual time the first indicating edge 38' of the target 22 enters the field 20 with the actual time that the second indicating edge 32' of the target 22 exited the field 20. The processor 18 is further configured to calculate the blade 17 frequency, -amplitude, and phase of vibration based upon the above two measurements.

Method of Assembly

Referring again to FIG. 1, the transmitter 16 of the monitoring system 10 may be mounted or installed within the cylinder wall of the inner cylinder 42 of a turbine generation. The transmitter 16 is advantageously located in the turbine wherever good transmission of the field 20 can be obtained. In the illustrated embodiment, the laser 16 is configured as part of a probe system having an external laser and produces a light beam 22 of a suitable wavelength is located in the inner cylinder wall 42 above the shroud 14 directed toward the blade 13 row to be monitored. However, the main requirement to be maintained is that the laser 16 transmits the light beam 20 and receives the reflected light beam 20'. Other locations are suitable, for example, any stationary component that offers a line of sight to the target 22 is acceptable. Furthermore, if the transmitter 16 is a laser 16, optical devices such as mirrors, lenses, fiber optic leads, and the like may be used from a remote location to aim and guide the light beam 20 to the target as well as receive the reflected beam 20'. In the illustrated embodiment, the laser 16 is located above the blade tip 28 oriented to point at the target 22. Additionally, a fiber optic cable may be used to carry and direct the light beam 20 to the target 22. As one skilled in the art would recognize, fiber optics lens such as a GRIN (gradient index) assembly may be used in conjunction with the fiber optic cable.

In the illustrated embodiment, the target 22 is oriented on the shroud 14 of a blade 17 with the base portion 32 of the triangle approximately parallel with the X-X axis 44. The portion of the right triangle perpendicular 34 to the base portion 32 is arranged approximately perpendicular to the X-X axis 44 and in the Z-Z direction 48. The length of the base portion 32 and the portion perpendicular 34 to the base portion can be adjusted to create a triangle hypotenuse 38 at the appropriate inclination. The basis of the measurement of the frequency and amplitude of blade vibration is determined from the difference in line length L1 36 of the non displaced shroud 14 as compared to the displaced line length L2 36' that results from the displaced target 22' on the displaced shroud 14' and is discussed in more detail below. The target 22 has a first indicating edge 38, 38' and a second indicating edge 32, 32'. As also indicated, the first indicating edge 38, 38' and the second indicating edge 32, 32' are non-parallel. The first indicating edge 38, 38' and the second indicating edge 38, 38' are identified by the direction of rotation 85 of the turbine shaft 70.

The target 22 is operatively connected with the blade 17. For example, the target 22 can be mounted on the shroud 14 or blade tip 28, painted the shroud 14 or blade tip 28, in contact with the blade 17, or attached to the blade 17. The means of connecting the target 22 with the blade 17 is in part a function of the field type generated by the transmitter 22. For example, if the transmitter 16 is a laser 16, the target 22 would be painted, sprayed, or mounted on the shroud 14 or blade tip 28. Alternatively, if a magnet 16 or microwave 16 is used as the transmitter, the shroud 14 would be advantageously adapted to reflect or otherwise alter, the field 20' by placing a groove or other suitable depression in the body of the shroud 14. The depression in the shroud 14 is necessary because of the nature of the field 20 generated by a magnetic transmitter 16 and a microwave transmitter 16. The depression or groove will closely match the exterior dimension and contour of the shroud 14 and can be formed into the shroud 14 in the shape of the target 22. If the blade 17 is produced from a nonferrous material, such as titanium, and the transmitter 16 is a magnet 16, then a target 22 capable of reflecting, or otherwise altering, the magnetic field 20' may be inserted in the shroud 14 depression. Moreover, the target 22 can be directly connected to the blade 17 or indirectly connected to the blade 17 via an interconnection. Suitable direct connections include, but are not limited to, adhesives, bolts, weldments, combinations thereof, and the like. Suitable interconnections include, but are not limited to a connective layer, an insulating layer, a damper, combinations thereof, and the like. However, as one skilled in the art will appreciate, the direct and indirect connections can be achieved in other ways to operatively associate the target 22 with the blade 17.

Method of Operation

In operation, as illustrated, after the monitoring system 10 is initiated, the laser 16 generates the light beam 20 that is transmitted toward the blade shroud 14. The transmitted light beam 20 creates a light spot on the shroud 14 that sweeps out a line 24 due to the rotation of the blades. The light spot functions as an indicator of the arrival and departure of the target 22. As the turbine blade 17 rotates in the Z-Z direction 48, the target 22 passes through the light beam 20 field and reflects at least a portion of the light beam field 20' back towards the receiver 50. The receiver 50 converts the reflected light beam 20' to a signal that is sent, by a suitable means such as telemetry, optical fiber, or wire, to the processor 18. The receiver 50 detects the reflected light beam 20' beginning when the first indicating edge 38' of the target 22 enters the field 20 until the second indicating edge 32' of the target 22 exits the field 20.

If the blade 17 is vibrating in one of the two fundamental directions, the shroud 14 will be located at a different position in the X-X and Z-Z plane for each revolution of the rotor 70. This is illustrated in FIG. 3a showing the shroud 14 and the displace shroud 14'. Lengths L1 36 and L2 36' are defined as the length of the light spot on the target 22 and the displaced target 22' respectively. The length L1 36 is determined from the time at which the second indicating edge 32 departs the field 20 subtracted from the time at which the first indicating edge 38 of the target 22 enters the field 20. Similarly, length L2 36' is determined from the time at which the second indicating edge 32 leaves the field 20 subtracted from the time at which the first indicating edge 38 of the target 22 enters the field 20. Thus, for example, if the blade is vibrating in the axial direction 44, length L1 36 and length L2 36' will be different and furthermore indicate the displacement of the target 22 in the X-X direction. Measurements over many revolutions of the shaft 70 thus produces a vibration wave of shroud 14 vibratory motion in the X-X direction. Vibration of the shroud 14 in the Z-Z direction has no affect on this differential time measurement. Likewise, if the blade 17 is vibrating in the tangential direction, Z-Z 48, or has a component of vibration in the Z-Z direction 48, the actual time the second indicating edge 32 leaves the field 20 is subtracted from a calculated of the second indicating edge 32. Measurements over many revolutions of the shaft 70 thus produces a vibration wave of vibratory motion in the Z-Z direction 48. The time at which the first indicating edge 38 of the target 22 enters the field 20 is not used in this measurements. Vibration of the shroud in the X-X direction 44 has no affect on this arriving time measurement.

The processor 18 then interprets the time sequences from the reflected light beam 20' accurately measured over an extended number of revolutions of the shaft 70. The processor 18 can convert time differences into displacements given the frequency of a suitable high frequency clock, preferably greater than 100 MHz, the rotation speed of the shaft 70, and radial (Y-Y direction 46) distance of the shroud 14 from the X-X axis 44. The processor 18 computes the frequency, amplitude, and phase of vibration of the rotating blade 17 from the sequence of time signals sent from the receiver 50 as described above. For example, an increase or decrease in the signal duration of the reflected light beam 20' enables displacement measurements in the X-X direction 44 and a deviation from the expected time of arrival of target 22 edge 32 indicates a displacement of the blade tip 28 in the Z-Z direction. Thus, the change in signal duration of the reflected light beam 52 and time of arrival of edge 32 compared to an expected value can be converted to a monitoring signal 60 on a visual display monitor 40. The two separately measured and orthogonal X-X and Z-Z displacements can be analyzed separately or combined into a single orbit of the blade's motion. A Fourier, or other suitable analysis of this signal provides the amplitude, frequency and phase of the vibration of blade 17 and all other blades in the row. Data can be interpreted and stored by the processor 18 in real time (i.e. instantaneously) or non real time (i.e. any time period greater than real time).

The processor 18 the outputs the calculations output in a form that suitably displays the processed information. A graphical output 40 advantageously allows the data 60 to be displayed in a user friendly fashion, such as a graph. Alternatively, the data 60 could be stored separately and used with a suitable program or database and analyzed at a later date. Lastly, the data 60 could be used and compared to other data 60 for the purpose of determining trends in the systems being monitored.

Although the illustrated embodiment shows the target 22 placed on each shroud 14 segment, the target 22 need not be placed on the shroud 14 of each blade 17 in the blade row 13. Rather, multiple blades 17 in the blade row 13 may be have a single target 22. However, because of geometric variances of the blades 17, placing a target 22 on the shroud 14 of each blade 17 in the blade row 13 will provide more accurate results. Additionally, the shrouded blade 17 permits placement of a larger target 22 improving the ability to more accurately measure blade tip 28 motion.

While the preferred embodiments of the present invention have been shown and described herein, it will be obvious that such embodiments are provided by way of example only. Numerous variations, changes and substitutions will occur to those of skill in the art without departing from the invention herein. Also, one or more aspects or features of one or more embodiments or examples of the present invention may be used or combined with one or more other embodiments or examples of the present invention. Accordingly, it is intended that the invention be limited only by the spirit and scope of the appended claims.

The invention claimed is:

1. A system for monitoring rotating blade vibration, comprising:
   a blade;
   a target with a first indicating edge and a second indicating edge, the first and second indicating edges being non-parallel and arranged on top of the blade;
   a receiving device adapted to receive data about the target to calculate an amplitude or phase of an axial or tangential mode of vibration; and
   a processor that interprets the received data or information from the receiving device over many revolutions of the blade to determine a vibration wave of vibratory motion of the blade.

2. The system as claimed in claim 1, wherein the receiving device transmits a field.

3. The system as claimed in claim 1, further comprising a transmitting device that generates a field that the target passes through.

4. The system as claimed in claim 3, wherein the transmitting device is selected from the group consisting of: a laser, a magnetic sensor, a microwave transmitter, and combinations thereof.

5. The system as claimed in claim 1, wherein the target geometry has two non-parallel edges.

6. The system as claimed in claim 5, wherein the target geometry is a triangle.

7. The system as claimed in claim 6, wherein the target geometry is a right triangle.

8. The system as claimed in claim 1, wherein the target is painted on a tip or shroud of the blade.

9. The system as claimed in claim 1, wherein the target is a fired ceramic coating on the tip or shroud of the blade.

10. The system as claimed in claim 1, wherein the target is adapted to reflect a laser beam.

11. The system as claimed in claim 1, wherein the target is located on a single blade.

12. The system as claimed in claim 1, wherein the target is located on a plurality of blades.

13. The system as claimed in claim 1, wherein a laser is surrounded by a plurality of receivers.

14. The system as claimed in claim 1, wherein the sensor is located above the target.

15. The system as claimed in claim 1, wherein a frequency, amplitude, and phase of an axial or tangential mode of vibration is calculated.

16. The system as claimed in claim 1, wherein a combined axial and tangential mode of vibration is calculated.

17. The system as claimed in claim 1, wherein the axial mode of vibration is individually calculated or the tangential mode of vibration is individually calculated.

18. The system as claimed in claim 1, wherein the amplitude or phase is the amplitude or phase of only the axial component of vibration and having no tangential component.

19. The system as claimed in claim 1, wherein the amplitude or phase is the amplitude or phase of only the tangential component of vibration and having no axial component.

20. A blade adapted for measuring blade vibration, comprising:
   a root portion;
   a platform portion;
   an airfoil portion; and
   a target with a first indicating edge and a second indicating edge, the first indicating edge and the second indicating edge being non-parallel,
   wherein a vibration wave of vibratory motion of the blade including an amplitude or phase is determined over many revolutions of the operating blade.

21. The blade as claimed in claim 20, wherein the blade is a shrouded blade.

22. The blade as claimed in claim 21, wherein the shroud is adapted to support a target.

23. The blade as claimed in claim 21, wherein the target has two non-parallel edges.

24. The blade as claimed in claim 21, wherein the target has the shape of a right triangle.

25. The blade as claimed in claim 20, wherein the amplitude or phase is the amplitude or phase of only the axial component of vibration and having no tangential component.

26. The blade as claimed in claim 20, wherein the amplitude or phase is the amplitude or phase of only the tangential component of vibration and having no axial component.

27. A method for monitoring vibration of a blade, comprising:
   connecting a target to a blade tip;
   passing the target through a first transmission signal field of a transmission device at a first moment in time;
   reflecting the transmission signal from the target to a receiver at a second moment in time; and
   processing the first and second received signals over many revolutions of the blade to obtain a vibration wave of vibratory motion of the blade.

28. The method as claimed in claim 27, wherein a frequency, amplitude, or phase of an axial or tangential mode of vibration is determined.

29. The method as claimed in claim 27, wherein a combined axial and tangential mode of vibration is determined.

* * * * *